United States Patent
Choi et al.

(10) Patent No.: US 9,629,796 B2
(45) Date of Patent: Apr. 25, 2017

(54) COLORED GLOSSY PIGMENT USING VEGETABLE TYPE NATURAL DYE AND METHOD FOR PREPARING SAME

(71) Applicant: CQV CO., LTD., Chungcheongbuk-do (KR)

(72) Inventors: Min Choi, Gwangju (KR); Kum-Sung Cho, Chungcheongbuk-do (KR); Kwang-Choong Kang, Cheongju-si (KR); Byung-Ki Choi, Cheongju-si (KR); Kwang-Soo Lim, Chungcheongbuk-do (KR); Kil-Wan Chang, Cheongju-si (KR)

(73) Assignee: CQV CO., LTD., Chungcheongbuk-Do (KR)

( * ) Notice: Subject to any disclaimer, the term of this patent is extended or adjusted under 35 U.S.C. 154(b) by 0 days.

(21) Appl. No.: 15/033,094

(22) PCT Filed: Oct. 28, 2014

(86) PCT No.: PCT/KR2014/010212
§ 371 (c)(1),
(2) Date: Apr. 28, 2016

(87) PCT Pub. No.: WO2015/065027
PCT Pub. Date: May 7, 2015

(65) Prior Publication Data
US 2016/0271052 A1    Sep. 22, 2016

(30) Foreign Application Priority Data
Oct. 28, 2013  (KR) .................. 10-2013-0128836

(51) Int. Cl.
*C09C 1/00* (2006.01)
*C09C 3/10* (2006.01)
(Continued)

(52) U.S. Cl.
CPC .................. *A61K 8/97* (2013.01); *A61K 8/25* (2013.01); *A61Q 1/02* (2013.01); *B05D 3/007* (2013.01);
(Continued)

(58) Field of Classification Search
CPC  C09C 1/00; C09C 3/10; C09C 1/0015; C09C 1/0036; C09C 1/0063; C09C 3/08;
(Continued)

(56) References Cited

U.S. PATENT DOCUMENTS

| 4,084,983 A | 4/1978 | Bernhard et al. |
| 4,274,830 A * | 6/1981 | Woznicki ............. A61K 9/2866 |
| | | 424/401 |

(Continued)

FOREIGN PATENT DOCUMENTS

| DE | 2928287 A1 | 1/1981 |
| JP | 52-146436 A * | 12/1977 |

(Continued)

OTHER PUBLICATIONS

Derwent-Acc-No. 2012-G50012, abstract of Brazilian Patent Specification No. BR 201004443 A2 (Feb. 2012).*
(Continued)

*Primary Examiner* — Anthony J Green
(74) *Attorney, Agent, or Firm* — Hauptman Ham, LLP

(57) ABSTRACT

The present invention relates to a method of preparing a colored gloss pigment using a natural dye. According to the present disclosure, the method may include preparing a dye from a dye material of natural dyes; titrating the dye with an inorganic salt solution and subsequently adjusting a pH neutral to prepare a natural pigment containing the dye; dispersing a substrate coated with a metal oxide into a DI water to form a substrate suspension; and introducing a pH adjusting agent and the natural pigment into the substrate (Continued)

suspension to coat a surface of the substrate with the natural pigment.

19 Claims, 5 Drawing Sheets

(51) Int. Cl.
| | | |
|---|---|---|
| A61K 8/97 | (2017.01) | |
| C09C 3/08 | (2006.01) | |
| C09B 61/00 | (2006.01) | |
| C09B 63/00 | (2006.01) | |
| C09B 67/38 | (2006.01) | |
| A61K 8/25 | (2006.01) | |
| A61Q 1/02 | (2006.01) | |
| B05D 3/00 | (2006.01) | |
| C09D 17/00 | (2006.01) | |

(52) U.S. Cl.
CPC ............ *C09B 61/00* (2013.01); *C09B 63/005* (2013.01); *C09B 67/008* (2013.01); *C09C 1/0015* (2013.01); *C09C 1/0036* (2013.01); *C09C 1/0063* (2013.01); *C09C 3/08* (2013.01); *C09D 17/001* (2013.01); *C09D 17/003* (2013.01); *A61K 2800/43* (2013.01); *A61K 2800/622* (2013.01); *A61K 2800/805* (2013.01); *C09C 2200/102* (2013.01)

(58) Field of Classification Search
CPC ...... C09C 2200/102; A61K 8/97; A61K 8/25; A61K 2800/43; A61K 2800/622; A61K 2800/805; A61Q 1/02; B05D 3/007; C09B 61/00; C09B 63/005; C09B 67/008; C09D 17/001; C09D 17/003
See application file for complete search history.

(56) References Cited

U.S. PATENT DOCUMENTS

| | | | | |
|---|---|---|---|---|
| 4,475,919 A | * | 10/1984 | Woznicki | ............ A61K 9/2866 426/250 |
| 5,061,317 A | * | 10/1991 | Korpi | .................... C09C 1/0015 106/417 |
| 5,344,486 A | * | 9/1994 | Mainz | .................. A61K 8/0216 106/415 |
| 7,052,541 B2 | * | 5/2006 | Chianelli | ............. C09D 7/1291 106/401 |
| 2003/0012753 A1 | | 1/2003 | Simon | |

FOREIGN PATENT DOCUMENTS

| | | | |
|---|---|---|---|
| JP | 52-148632 A | * | 12/1977 |
| KR | 10-2004-0006080 A | | 1/2004 |
| KR | 10-0743674 B1 | | 7/2007 |
| KR | 10-2011-0054099 A | | 5/2011 |
| KR | 10-2011-0073743 A | | 6/2011 |
| KR | 10-1135360 B1 | | 4/2012 |
| WO | 2004/033563 A2 | | 4/2004 |
| WO | WO 2009/092104 A1 | * | 7/2009 |

OTHER PUBLICATIONS

Derwent-Acc-No. 2011-K53193, abstract of Korean Patent Application No. KR 2011073743 A (Jun. 2011).*
International Search Report mailed Jan. 20, 2015 corresponding to International Application No. PCT/KR2014/010212.
European Search Report for corresponding European Patent Application No. 14858142.4 issued on Sep. 19, 2016.

* cited by examiner

COLORED GLOSSY PIGMENT USING VEGETABLE TYPE NATURAL DYE AND METHOD FOR PREPARING SAME

CROSS REFERENCE TO RELATED APPLICATION

This application claims the priority of Korean Patent Application No. 10-2013-0128836, filed on Oct. 28, 2013 in the KIPO (Korean Intellectual Property Office). Further, this application is the National Phase application of International Application No. PCT/KR2014/010212 filed Oct. 28, 2014, which designates the United States and was published in Korean.

BACKGROUND

Technical Field

The present invention relates to a manufacture of a colored gloss pigment, and more particularly, to a colored gloss pigment for cosmetics using a natural vegetable dye, and the preparation thereof.

Background Art

Organic pigments offer a wide range of brilliant colors and an excellent coloring power, but are much more expensive and have poor durability and heat resistance than inorganic pigments.

As environmental problems have become serious in recent years, the recent trend has been largely in favor of using the organic pigments compared to the inorganic pigments. The organic pigments are mainly used in paints, ink, rubber, textiles, paper, leather, cosmetics, and the like.

Among these, cosmetic pigments are highly sensitive to the changing trends and so a variety of products are constantly available in the market. However, there are lots of restrictions imposed on raw materials due to environmental regulations. Accordingly, there currently exists a demand in the market for cosmetic pigments with new types of natural organic pigments.

Cosmetic products are largely classified into base makeup products used for applying over an entire face and point makeup products used for applying a local part of the face. The point makeup products are used for the purpose of imparting a luxurious feeling on the face with lipstick, eye shadow, brush, etc. to look beautiful. For such cosmetic products, color is the most important factor.

Up to date, one of the raw materials most commonly used in cosmetics to express a red color is carmine. Carmine is an animal red pigment which is prepared by drying a cochineal insect parasitic on a cactus to make a powder. Carmine is widely used as a pigment for red color in cosmetics, beverage, ice cream, etc. Carmine may cause allergic reactions including urticaria, rhinitis, or asthma, depending on the person, and also may cause hyperactivity disorder to children.

Accordingly, development of pigment with a natural vegetable dye for cosmetics which can exhibit a red color in place of the carmine, and further with a natural vegetable dye which can exhibit a color such as blue or green is required.

In the related background art to the present disclosure, the Korea Patent No. 0743674 (Issuance Date: Jul. 23, 2007) discloses a pearlescent pigment and a preparation method thereof.

DISCLOSURE

An object of the present disclosure is to provide a method of preparing a colored gloss pigment for cosmetics which is human body-friendly and nature-friendly by preparing a colored pigment with a natural dye and coating the pigment on a substrate.

In order to accomplish the above object, there is provided a method of preparing a colored gloss pigment with a natural dye in accordance with an aspect of the present disclosure, which may include preparing a dye from a dye material of red series, purple series, or black series of natural dyes; titrating the dye with an inorganic salt solution and subsequently adjusting a pH neutral to prepare a natural pigment containing the dye; introducing a flake substrate into a deionized water (DI water) with stirring for dispersion to form a substrate suspension; and introducing a pH adjusting agent and the natural pigment into the substrate suspension to coat a surface of the flake substrate with the natural pigment.

In order to accomplish the above object, there is provided a method of preparing a colored gloss pigment with a natural dye in accordance with another aspect of the present disclosure, which may include preparing a natural pigment from a blue series of natural dyes; introducing a deionized water (DI water) into the natural pigment and subjecting to a ball milling to form natural pigment particles; mixing the natural pigment particles, the DI water, and a flake substrate with stirring for dispersion to form a substrate suspension; and titrating the substrate suspension with an inorganic solution to adjust a pH with stirring to coat a surface of the flake substrate with the natural pigment.

According to the present disclosure, a human body-friendly and nature-friendly colored gloss pigments can be provided using a red series, a purple series, a yellow series, a blue series, a green series, or black series of natural dyes.

Accordingly, the natural vegetable pigments can replace the animal organic pigment such as carmine, and reduce the environmental pollutions due to chemicals during the production of cosmetics, as well as can be applied to hypoallergenic cosmetics in nature.

BRIEF DESCRIPTION OF THE DRAWINGS

The above and other objects and features of the present disclosure will become apparent from the following description of the disclosure, when taken in conjunction with the accompanying drawings, in which.

BEST MODE

Hereinafter, a colored gloss pigment with a red series, yellow series, blue series, green series, purple series, or black series of natural dyes in accordance with an embodiment of the present disclosure, and its preparation method will be described.

Figure 1:
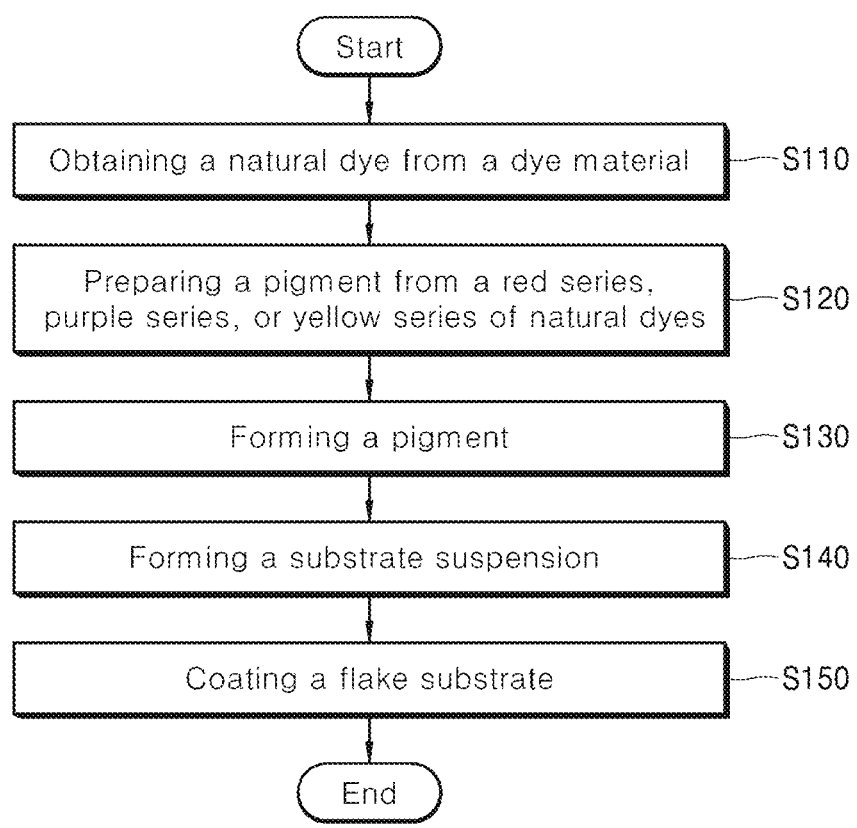
FIG. 1 is a flow diagram illustrating a method of preparing a colored gloss pigment with a red series, yellow series, purple series, green series, or black series of natural dyes in accordance with an embodiment of the present disclosure.

FIG. 1 is a flow diagram illustrating a method of preparing a colored gloss pigment with a red series, yellow series, purple series, green series, or black series of natural dyes in accordance with an embodiment of the present disclosure.

Referring to FIG. 1, the method of preparing a colored gloss pigment with a natural dye in accordance with an embodiment of the present disclosure may include preparing a natural dye from a dye material (S110); titrating the natural dye with an inorganic salt solution and subsequently adjusting a pH neutral to prepare a natural pigment containing the natural dye (S120, S130); introducing a flake substrate including at least one of synthetic mica, natural mica, glass, plate-like iron oxide, plate-like alumina, plate-like silica, talc, or bismuth, and a pigment composition containing a metal oxide into a deionized water (DI water) with stirring for dispersion to form a substrate suspension (S140); and introducing a pH adjusting agent and the natural pigment into the substrate suspension to coat a surface of the flake substrate with the natural pigment (S150).

The step of preparing a natural dye (S110) may include adding and heating 10 to 30 parts by weight of a natural dye based on 100 parts by weight of DI water or an organic solvent to extract a salt solution, and concentrating and drying in a vacuum the salt solution. In this embodiment, the natural dye may be of a red series, yellow series, purple series, blue series, green series, or black series.

Further, the dye material of the natural dye may be of at least one red or purple series selected from the group consisting of madder, safflower, sappanwood, logwood, gromwell, persimmon, apricot, plum, *Euonymus sachalinensis, Lindera obtusiloba*, Ginger roots, *Althaea rosea Cavanil, Fallopia japonica, Pinus densiflora, Taxus, Schisandra, Camellia*, grapes, *Betula platyphylla*, and combinations thereof, or at least one yellow or green series selected from the group consisting of *Gardenia jasminoides, Curcuma longa, Allium cepa, Safflower yellow, Coptis, Phellodindron, Syzygium aromaticum, Punica granatum, Phragmites australis, Sopbora Japonica L., Fraxinus rhynchophylla, Toxicodendron vernicifluum, Caesalpinia sappan, Sorbus alnifolia, Forsythia koreana, Campsis granditlora, Alnus japonica, Castanea crenata, Quercus acutissima*, and combinations thereof.

The step of preparing a natural pigment (S120) may include adding to the dye a metal salt containing solution in dropwise to form a mixed solution of the dye and the metal salt, stirring the mixed solution of the dye and the metal salt, dipping pigment particles into the mixed solution of the dye and the metal salt, and separating the dipped pigment particles and drying the same.

In the step of preparing the mixed solution of the dye and the metal salt, the metal salt may include a mixture comprising at least one selected from the group consisting of $BaCl_2$, $CaCl_2$, $AlCl_3$, $SnCl_4$, $TiCl_4$, $TiOCl_2$, $TiOSO_4$, $FeCl_3$, $FeSO_4$, $SlCl_4$, $ZrOCl_2$, $Na_2O.SiO_2.5H_2O$, $MnCl_2$, $MgCl_2$, and $CoCl_2$.

The mixed solution of the dye and the metal salt is prepared such that it comprises 100 parts by weight of the deionized water, 3 to 30 parts by weight of the dye, and 3 to 30 parts by weight of the metal salt.

Then, the mixed solution of the dye and the metal salt is stirred. The mixed solution of the dye and the metal salt is heated with stirring at 20° C. to 60° C. and at 200 rpm to 300 rpm. At this time, a basic solution comprising a mixture of at least one selected from the group consisting of NaOH, KOH, $Ca(OH)_2$, $NH_3$, $Mg(OH)_2$, $CH_3NH_2$, $CH_3CH_2NH_2$, $CH_3OH$, and $Al(OH)_3$ is added to the mixed solution of the dye and the metal salt to adjust pH, allowing the immersion of the pigment particles. At the temperature less than 40° C., the efficiency of the reaction is reduced, while at the temperature above 60° C., the color of the pigment may change.

Then, the dipped pigment particles are separated and dried.

The step of forming the pigment particles (S130) may include milling the prepared natural pigment, and mixing the pigment into the DI water with stirring for dispersion.

In milling the pigment, it is preferred that the pigment is sufficiently milled at 50 rpm to 2000 rpm for about 12 hours to about 24 hours.

For example, the milling balls may constitute 300 mL of 500 mL in volume. If the volume of the milling balls is less than 300 mL, the milling efficiency is reduced and the agglomerated pigment particles are not evenly distributed. Whereas, if the volume of the milling balls is greater than 300 mL, the milling is relatively less efficient since the amount of the pigment that can be placed inside the vessel is less than that of the milling balls. The milling is carried out for at least 12 hours up to 24 hours. When the milling is conducted at less than 50 rpm, the dispersion effects are reduced, whereas when the milling is conducted at greater than 2000 rpm, the pigment particles may be damaged. For the quality of the pigment, it is important to improve the dispersion of the pigment particles under appropriate rpm conditions.

The step of forming a substrate suspension (S140) may include introducing a flake substrate into the DI water with stirring for dispersion. The flake substrate may include one or more of synthetic mica, natural mica, glass, plate-like iron oxide, plate-like alumina, plate-like silica, talc, or bismuth. In addition, the flake substrate may be coated with a metal oxide. This step may be carried out at 200 rpm to 500 rpm.

In the step of coating the natural pigment (S150), a pH adjusting agent and the natural pigment is mixed into the substrate suspension formed in the step (S140) to coat a surface of the flake substrate with pigment particles in which natural vegetable dye components are contained. In this embodiment, the pH adjusting agent may be an acidic solution comprising a mixture of at least one selected from hydrochloric acid, sulfuric acid, and acetic acid.

In the step of coating the natural pigment (S150), the pH of the mixed solution of the substrate suspension and the natural pigment is adjusted to 4.0 to 8.0, and the coating reaction is preferably carried out at 200 rpm to 500 rpm for 30 minutes to 60 minutes.

After the step (S150), further included is washing and dehydrating the flake substrate coated with an oxide layer, drying the washed flake substrate, and screening/separating a flake substrate formed larger than a predetermined size among the flake substrates using a mesh.

The step of drying the flake substrate may be carried out at 60° C. to 100° C. for 12 hours to 24 hours.

In the step of screening the flake substrate, the separated flake substrate may be not greater than 45 μm.

In the step of the screening, the mesh may be used to remove agglomerated particles resulting from the reaction.

Further, hereinafter, a colored gloss pigment with a blue series or a green series of natural dyes in accordance with another embodiment of the present disclosure and its preparation method will be described.

Figure 2:
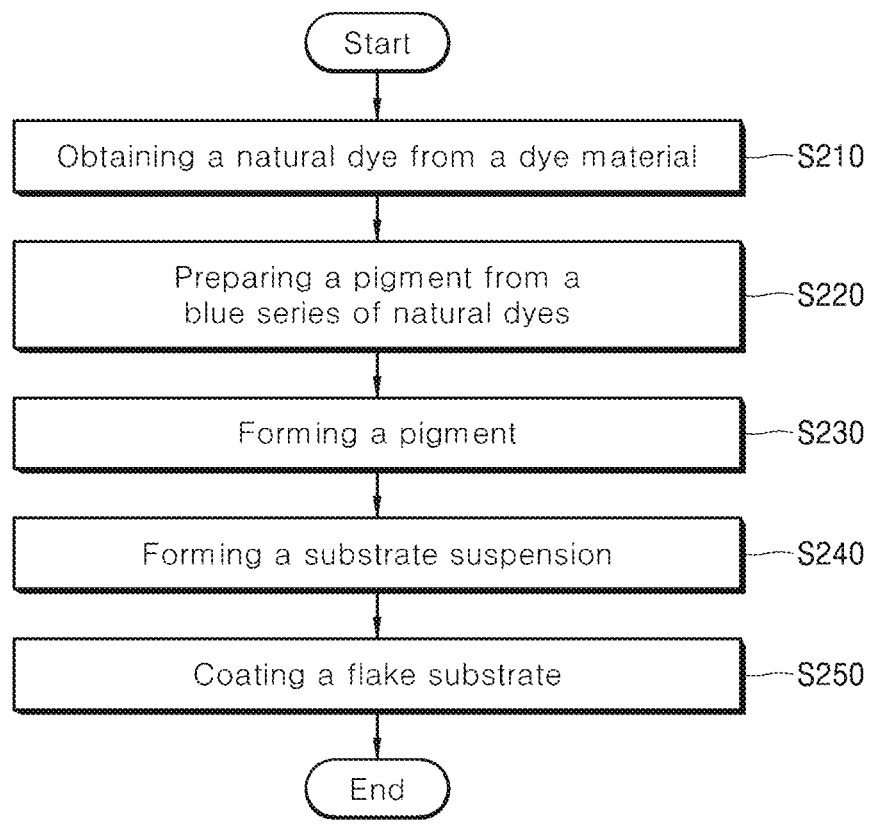
FIG. 2 is a flow diagram illustrating a method of preparing a colored gloss pigment with a blue or green series of natural dyes in accordance with another embodiment of the present disclosure.

FIG. 2 is a flow diagram illustrating a method of preparing a colored gloss pigment with a blue or green series of natural dyes in accordance with another embodiment of the present disclosure.

Referring to FIG. 2, the method of preparing a colored gloss pigment with a blue or green series of natural dyes in accordance with another embodiment of the present disclosure may include preparing a natural dye from a dye material (S210); preparing a natural pigment from a blue series of natural dyes (S220); introducing a deionized water (DI water) into the natural pigment and subjecting to a ball milling to form natural pigment particles (S230); mixing a flake substrate, the natural pigment particles, and the DI water, with stirring for dispersion, to form a substrate suspension (S240); and titrating the substrate suspension with an inorganic solution to adjust a pH with stirring to coat a surface of the flake substrate with the natural pigment (S250).

The step of preparing a natural dye (S210) may include adding and heating 5 to 30 parts by weight of a natural dye based on 100 parts by weight of DI water or an organic solvent to extract a salt solution, and concentrating and drying in a vacuum the salt solution.

In this embodiment, the natural dye may be of a blue or green series. To this end, a dye material of the natural dyes may be of at least blue or green series selected from indigo, *Commelina communis*, *Iris sanguinea*, and combinations thereof.

Then, in the step of preparing a natural pigment (S220), the natural pigment is prepared from a blue series of natural dyes. This step may be carried out as in the natural pigment preparation process shown in FIG. 1, but the step of forming the natural pigment particles (S230) may be directly carried out without conducting this step.

In the step of forming the natural pigment particles (S230), the natural pigment is preferably contained in a range of 10 parts by weight to 30 parts by weight based on 100 parts by weight of the DI water.

If the natural pigment is contained less than 10 parts by weight, the reaction efficiency may be reduced due to the low concentration, whereas if it exceeds 30 parts by weight, the reaction efficiency may also be deteriorated due to the excessive amount of the natural pigment relative to the reaction solution.

Meanwhile, in the step of forming the natural pigment particle (S230), the ball-milling may preferably be carried out for 6 hours to 12 hours.

If the ball milling time is less than 6 hours, the dispersion may be insufficient, and if it exceeds 12 hours, only the process time may take longer without any further dispersion effect, so less efficient.

In the step of forming a substrate suspension (S240), the substrate may preferably have an average particle diameter of 2 to 250 μm, and have a thickness of 0.2 to 5 μm.

The substrate may include one or more of synthetic mica, soft mica, glass, plate-like iron oxide, plate-like alumina, plate-like silica, talc, or bismuth. In addition, the flake substrate may be coated with a metal oxide.

If the average particle diameter is less than 2 μm, the same color constantly having a same refractive index cannot be represented due to a light scattering by a reduced aspect ratio, whereas if it exceeds 250 μm, it may be difficult to form an oxide layer for implementing a color due to an increase in the surface area to be coated.

In this embodiment, the substrate may preferably be contained in a range of 3 parts by weight to 15 parts by weight based on 100 parts by weight of the substrate suspension.

If the concentration of the substrate is less than 3 parts by weight, the concentration is too low and so can decrease the reaction efficiency, whereas if it exceeds 15 parts by weight, some aggregation may be caused due to the deep concentration.

In this embodiment, the stirring may be preferably performed at room temperature at a stirring speed of 200 rpm to 500 rpm.

If the stirring speed is less than 200 rpm, the pigments may be aggregated due to a poor dispersing effect during the reaction, whereas if it exceeds 500 rpm, only rpm becomes higher without any dispersion effect and so the efficiency could be lower.

In the step of coating the natural pigment (S250), the substrate suspension is titrated with an inorganic salt solution to adjust the pH of the substrate suspension and is stirred to coat a surface of the flake substrate with the natural pigment.

In this embodiment, the pH may be adjusted by at least two pH adjustment steps as below.

The pH adjustment step may include (i) a first pH adjustment step, which involves slowly titrating the substrate suspension with 5% by volume concentration of a metal salt 1, and stirring for 5 minutes to 30 minutes, to adjust the pH to 7 to 7.1; (ii) a second pH adjustment step, which involves slowly titrating with 5% by volume concentration of a metal salts 2, and stirring for 5 minutes to 30 minutes, to adjust the pH to 4 to 4.1; (iii) a third pH adjustment step, which involves slowly titrating with 15% by volume concentration of HCl solution, and stirring for 5 minutes to 30 minutes, to adjust the pH to 2.1 to 2.2; and a fourth pH adjustment step, which involves slowly titrating with 15% by volume concentration of a basic solution, and stirring for 5 minutes to 30 minutes, to adjust the pH to 4.2 to 4.4.

After the step of coating the natural pigment (S250), the present method may further include washing and dehydrating the flake substrate coated with the natural pigment, drying the washed flake substrate, and screening/separating the flake substrate formed larger than a predetermined size of the flake substrate among the flake substrate as dried using a mesh.

The drying of the flake substrate may be carried out at 60° C. to 100° C. for 6 hours to 12 hours.

In the step of screening of the flake substrate, the separated flake substrate may be less than or equal to 45 μm.

In the step of screening the flake substrate, the aggregated particles resulting from the reaction may be removed using a mesh.

In accordance with the present disclosure, a human body-friendly and nature-friendly colored gloss pigment may be provided using a red series, purple series, yellow series, blue series, green series, or black series of natural dyes.

Accordingly, the natural vegetable pigments can replace the conventional animal organic pigment such as carmine, and reduce the environmental pollutions due to chemicals during the production of cosmetics, as well as can be applied to hypoallergenic cosmetics in nature.

Hereinafter, the present disclosure will be described in detail through preferred embodiments thereof. The preferred embodiments will be set forth for illustration purposes only, but cannot be construed as limiting the disclosure in any sense.

It is understood that the information which is not specifically described herein can be sufficiently inferred by those skilled in the art, and therefore the descriptions on such information will be omitted.

EXAMPLES

Example 1

Preparation of Red Series of Natural Pigment (1) Preparation of Natural Red Pigment A natural dye extracted from *Caesalpinia sappan* which is a dye material of the natural dye (including at least one mixture selected from *Caesalpinia sappan* bark extract, or *Caesalpinia sappan* stem powder) was heated in a deionized water (or organic solvent), and the extracted dye solution was concentrated and dried in a vacuum to prepare a dye. 10 parts by weight of the dye of *Caesalpinia sappan* was transferred into a 2 L beaker, and 100 parts by weight of deionized water and 30 parts by weight of $CaCl_2$ was introduced thereinto and stirred at 200 rpm. At this time, the reaction temperature was set to 40° C. and potassium hydroxide was added. pH was adjusted to 7. Once precipitates were generated while stirring the solution, the precipitates were dehydrated, dried and then ground for use as a pigment.

(2) Preparation of Natural Red Pigment Ink

To a 500 mL beaker, 140 parts by weight of deionized water and 60 parts by weight of *Caesalpinia sappan* pigment were added, and subjected to a milling at 70 rpm for 12 hours, to form the *Caesalpinia sappan* pigment.

(3) Coating a Substrate using the Natural Red Pigment

To a 2 L beaker, 100 parts by weight of flake substrate and 1,000 parts by weight of deionized water were added, and then dispersed at 400 rpm to form a substrate suspension. At this time, the reaction was carried out at room temperature.

To the *Caesalpinia sappan* pigment, potassium hydroxide was added to adjust the pH to 11.

To the 2 L beaker, the substrate suspension, the *Caesalpinia sappan* pigment, and $CaCl_2$ were added to adjust the pH of the mixed solution back to 5.

After coating a mica substrate with the *Caesalpinia sappan* pigment, stirring was conducted for approximately 10 minutes, and then the reaction was completed.

After coating the same with the red *Caesalpinia sappan* pigment, water washing and dehydrating were conducted, and dried at 80° C. As a result, the mica coated with the red *Caesalpinia sappan* pigment was produced.

After completion of drying, a sieve of 325 meshes was used to screen/remove aggregated particles resulting from the reaction.

Figure 4:
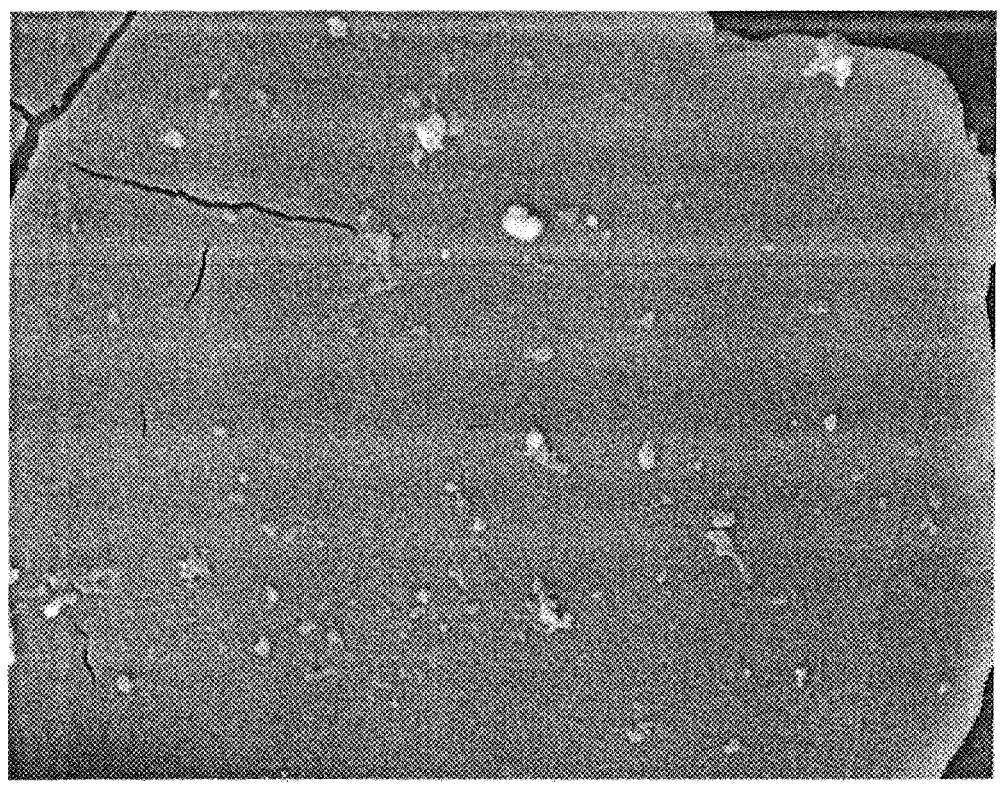

FIG. 4 is a SEM image of a substrate coated with a colored gloss pigment using a natural red dye prepared in accordance with this example.

Example 2

Preparation of Yellow Series of Natural Pigment (1) Preparation of Natural Yellow Pigment A natural dye extracted from *Gardenia jasminoides* which is a dye material of the natural dye was heated in a deionized water (or organic solvent), and the extracted dye solution was concentrated and dried in a vacuum to prepare a dye. 20 parts by weight of the dye of *Gardenia jasminoides* was transferred into a 2 L beaker, and 100 parts by weight of deionized water and 30 parts by weight of $AlCl_3$ was introduced thereinto and stirred at 200 rpm. At this time, the reaction temperature was set to 60° C. and sodium hydroxide was added. pH was adjusted to 7. Once precipitates were generated while stirring the solution, the precipitates were dehydrated, dried and then ground for use as a pigment.

(2) Preparation of Natural Yellow Pigment Ink

To a 500 mL beaker, 140 parts by weight of deionized water and 60 parts by weight of *Gardenia jasminoides* pigment were added, and subjected to a milling at 70 rpm for 12 hours, to form the *Gardenia jasminoides* pigment.

(3) Coating a Substrate with the Natural Yellow Pigment

To a 2 L beaker, 100 parts by weight of flake substrate and 1,000 parts by weight of deionized water were added, and then dispersed at 400 rpm to form a substrate suspension. At this time, the reaction was carried out at room temperature.

To the *Gardenia jasminoides* pigment, potassium hydroxide was added to adjust the pH to 11.

To the 2 L beaker, the substrate suspension, the *Gardenia jasminoides* pigment, and $CaCl_2$ were added to adjust the pH of the mixed solution back to 5.

After coating a mica substrate with the *Gardenia jasminoides* pigment, stirring was conducted for approximately 10 minutes, and then the reaction was completed.

After coating the same with the yellow *Gardenia jasminoides* pigment, water washing and dehydrating were conducted, and dried at 80° C. As a result, the mica coated with the red *Gardenia jasminoides* pigment was produced.

After completion of drying, a sieve of 325 meshes was used to screen/remove aggregated particles resulting from the reaction.

Figure 3:
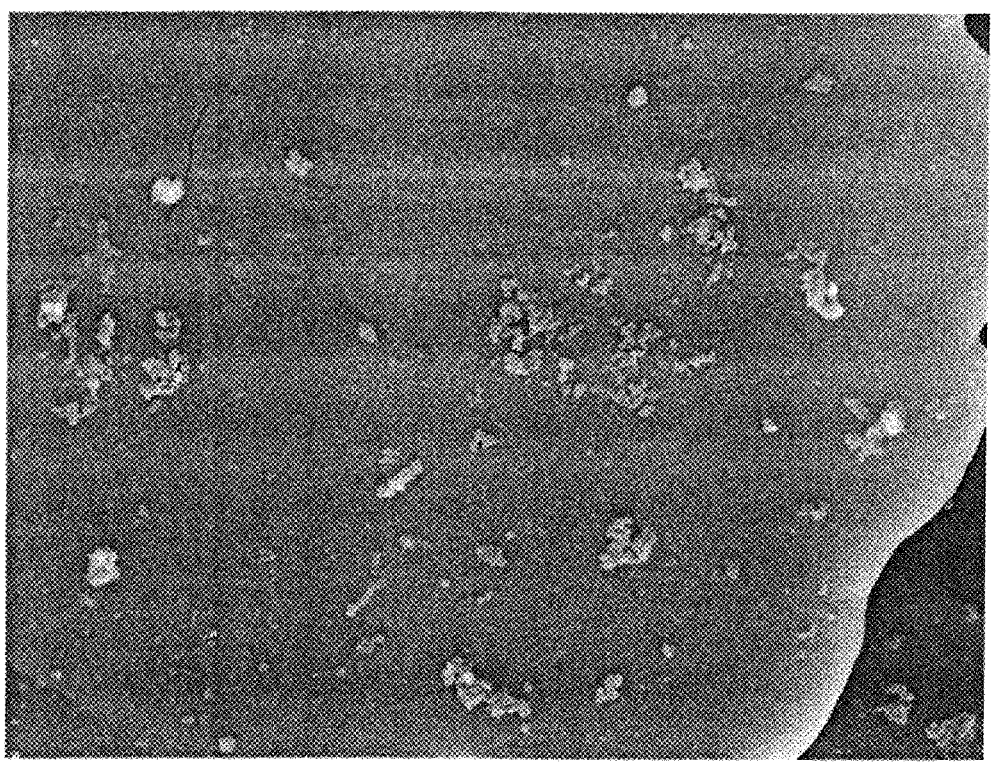
FIGS. 3 to 5 are SEM images of a substrate coated with a colored gloss pigment using a natural dye prepared in accordance with an embodiment of the present disclosure.

FIG. 3 is a SEM image of a substrate coated with a colored gloss pigment using a natural yellow dye prepared in accordance with this example.

Example 3

Preparation of Natural Blue Series Pigment (1) Preparation of Natural Blue Pigment/Natural Blue Pigment Ink A natural dye extracted from *Persicaria tinctorium* which is a dye material of the natural dye was heated in a deionized water (or organic solvent), and the extracted dye solution was concentrated and dried in a vacuum to prepare a dye. 20 parts by weight of the dye of *Persicaria tinctorium* was transferred into a 250 mL bottle for ball milling, and 80 parts by weight of deionized water was introduced thereinto and then subjected to a ball milling, to prepare *Persicaria tinctorium* pigment particles.

(2) Coating a Substrate with the Natural Blue Pigment

To a 2 L beaker, 30 parts by weight of mica and 20% by volume concentration of *Persicaria tinctorium* pigment particles were added, and deionized water was introduced thereinto to become a total 100 parts by weight, and then dispersed at 400 rpm to form a substrate suspension. At this time, the reaction was carried out at room temperature.

The substrate suspension was slowly titrated with 5% by volume concentration of $AlCl_3$ solution and was stirred for 10 minutes to adjust the pH to 7.0, and then slowly titrated with 5% by volume concentration of $CaCl_2$ solution and stirred for 10 minutes to adjust the pH to 4.0, and then slowly titrated with 15% by volume concentration of HCl solution and stirred for 30 minutes to adjust the pH to 2.2, and finally slowly titrated with 15% by volume concentration of KOH solution and stirred for 30 minutes to adjust the pH to 4.3, After coating a mica substrate with the *Persicaria tinctorium* pigment, stirring was conducted for approximately 10 minutes, and then the reaction was completed.

After coating the same with the natural blue *Persicaria tinctorium* pigment, water washing and dehydrating were conducted, and dried at 80° C. As a result, the mica coated with the blue *Persicaria tinctorium* pigment was produced.

After completion of drying, a sieve of 325 meshes was used to screen/remove aggregated particles resulting from the reaction.

Figure 5:
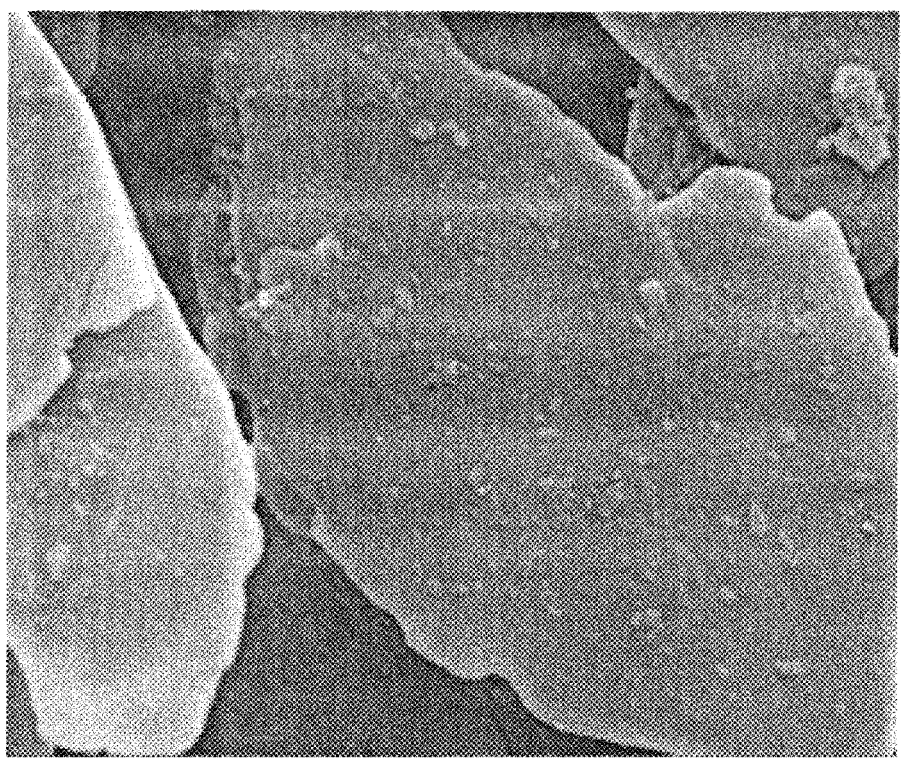

FIG. 5 is a SEM image of a substrate coated with a colored gloss pigment using a natural blue dye prepared in accordance with this example.

The invention claimed is:

1. A method of preparing a colored gloss pigment with a natural dye, comprising:
   preparing a dye from a dye material of red series, purple series, yellow series, or black series of natural dye;
   titrating the dye with an inorganic salt solution and subsequently adjusting a pH neutral to prepare a natural pigment containing the dye;
   introducing a flake substrate into a deionized water (DI water) with stirring for dispersion to form a substrate suspension; and
   introducing a pH adjusting agent and the natural pigment into the substrate suspension to coat a surface of the flake substrate with the natural pigment.

2. The method of claim 1, wherein in the step of preparing a dye, the dye material of the natural dye is of at least one red or purple series selected from the group consisting of madder, safflower, sappanwood, logwood, gromwell, persimmon, apricot, plum, *Euonymus sachalinensis, Lindera obtusiloba*, Ginger roots, *Althaea rosea Cavanil, Fallopia japonica, Pinus densiflora, Taxus, Schisandra, Camellia*, grapes, *Betula platyphylla*, and combinations thereof, or at least one yellow series selected from the group consisting of *Gardenia jasminoides, Curcuma longa, Allium cepa, Safflower yellow, Coptis, Phellodindron, Syzygium aromaticum, Punica granatum, Phragmites australis, Sopbora Japonica L., Fraxinus rhynchophylla, Toxicodendron vernicifluum, Caesalpinia sappan, Sorbus alnifolia, Forsythia koreana, Campsis granditlora, Alnus japonica, Castanea crenata, Quercus acutissima*, and combinations thereof.

3. The method of claim 1, wherein the step of preparing a dye further comprises:
   adding a DI water or an organic solvent to the dye material of the natural dye with heating to extract a salt solution; and
   concentrating the extracted salt solution and drying in a vacuum.

4. The method of claim 1, wherein the step of preparing a natural pigment further comprises:
   adding to the dye a metal salt containing solution in dropwise to prepare a mixed solution of the dye and the metal salt,
   stirring the mixed solution of the dye and the metal salt,
   dipping pigment particles into the mixed solution of the dye and the metal salt, and
   separating the dipped pigment particles and subsequently drying.

5. The method of claim 4, wherein the metal salt comprises at least one selected from the group consisting of $BaCl_2$, $CaCl_2$, $AlCl_3$, $SnCl_4$, $TiCl_4$, $TiOCl_2$, $TiOSO_4$, $FeCl_3$, $FeSO_4$, $SiCl_4$, $ZrOCl_2$, $Na_2O \cdot SiO_2 \cdot 5H_2O$, $MnCl_2$, $MgCl_2$ and $CoCl_2$, and the mixed solution of the dye and the metal salt comprises 100 parts by weight of the deionized water, 3 parts by weight to 30 parts by weight of the dye, and 10 parts by weight to 30 parts by weight of the metal salt.

6. The method of claim 4, wherein the step of stirring the mixed solution of the dye and the metal salt is carried out at a temperature of 20° C. to 60° C. and at a stirring speed of 200 rpm to 300 rpm, and comprises adding to the mixed solution of the dye and the metal salt, while stirring, a basic solution comprising a mixture of at least one selected from the group consisting of NaOH, KOH, $Ca(OH)_2$, $NH_3$, $Mg(OH)_2$, $CH_3NH_2$, $CH_3CH_2NH_2$, $CH_3OH$, and $Al(OH)_3$, wherein the basic solution is added to adjust a pH of the mixed solution of the dye and the metal salt to about 5 to about 7.

7. The method of claim 1, wherein the step of preparing a natural pigment further comprises:
   milling the prepared natural pigment; and
   mixing the milled natural pigment into a deionized water, and then stirring for dispersion.

8. The method of claim 1, wherein the step of forming a substrate suspension is carried out at 200 rpm to 500 rpm.

9. The method of claim 1, wherein the step of coating the natural pigment is carried out at pH of 4.0 to 8.0.

10. The method of claim 1, wherein the step of coating the natural pigment is carried out at 200 rpm to 500 rpm.

11. The method of claim 1, after the step of coating the natural pigment, further comprising:
    washing and dehydrating the flake substrate coated with the natural pigment;
    drying the washed flake substrate; and
    screening/separating the flake substrate formed according to size of the flake substrate using a mesh.

12. The method of claim 11, wherein the step of drying the flake substrate is carried out at a temperature of 60° C. to 100° C., and wherein in the step of screening the flake substrate, the separated flake substrate is not greater than 45 µm.

13. A method of preparing a colored gloss pigment with a natural dye, comprising:
    preparing a natural pigment from a blue series of natural dye;
    introducing a deionized water (DI water) into the natural pigment and subjecting to a ball milling to form natural pigment particles;
    mixing the natural pigment particles, a flake substrate and the DI water, with stirring for dispersion, to form a substrate suspension; and
    titrating the substrate suspension with an inorganic solution to adjust a pH with stirring to coat a surface of the flake substrate with the natural pigment.

14. The method of claim 13, wherein in the step of preparing a natural pigment, a dye material of the natural dye is of at least blue or green series selected from the group consisting of indigo, *Commelina communis, Iris sanguinea*, and combinations thereof.

15. The method of claim 13, wherein in the step of forming natural pigment particles, the natural pigment is contained in a range of 10 parts by weight to 30 parts by weight based on 100 parts by weight of the DI water.

16. The method of claim 13, wherein in the step of forming a substrate suspension, the substrate has an average particle diameter of 2 to 250 µm and a thickness of 0.2 to 5 µm, and the substrate is contained in a range of 3 parts by weight to 15 parts by weight based on 100 parts by weight of the substrate suspension.

17. The method of claim 13, wherein in the step of forming a substrate suspension, the stirring is carried out at an ambient temperature and at a stirring speed of 200 rpm to 500 rpm.

18. The method of claim 13, wherein in the step of coating with the natural pigment, the pH is adjusted by at least two pH adjustment steps, the pH adjustment step comprising:
    (i) a first pH adjustment step, which involves slowly titrating the substrate suspension with 5% by volume concentration of $AlCl_3$ solution, and stirring for 5 minutes to 30 minutes, to adjust the pH to 7 to 7.1;
(ii) a second pH adjustment step, which involves slowly titrating with 5% by volume concentration of $CaCl_2$ solution, and stirring for 5 minutes to 30 minutes, to adjust the pH to 4 to 4.1;
(iii) a third pH adjustment step, which involves slowly titrating with 15% by volume concentration of HCl solution, and stirring for 5 minutes to 30 minutes, to adjust the pH to 2.1 to 2.2; and
(iv) a fourth pH adjustment step, which involves slowly titrating with 15% by volume concentration of KOH solution, and stirring for 5 minutes to 30 minutes, to adjust the pH to 4.2 to 4.4.

19. The method of claim 13, after the step of coating the natural pigment, further comprising:
washing and dehydrating the flake substrate coated with the natural pigment;
drying the washed flake substrate; and
screening/separating the flake substrate formed according to the size of the flake substrate using a mesh,
wherein the step of drying the washed flake substrate is carried out at a temperature of 60° C. to 100° C. for certain period of time.

* * * * *